US006756050B2

(12) United States Patent
Cheung

(10) Patent No.: US 6,756,050 B2
(45) Date of Patent: Jun. 29, 2004

(54) DIETARY SUPPLEMENTS FOR IMPROVING MEMORY

(75) Inventor: Larry Ling Yuk Cheung, New Territories (HK)

(73) Assignee: Ultra Biotech Limited, Douglas (GB)

( * ) Notice: Subject to any disclaimer, the term of this patent is extended or adjusted under 35 U.S.C. 154(b) by 0 days.

(21) Appl. No.: 10/187,469

(22) Filed: Jun. 28, 2002

(65) Prior Publication Data

US 2004/0001861 A1 Jan. 1, 2004

(51) Int. Cl.[7] .................. A61K 47/00; C12N 13/00; C12N 1/14; C12N 1/16; C12N 1/18
(52) U.S. Cl. ............... 424/439; 424/400; 424/464; 424/489; 424/780; 424/800; 435/173.1; 435/173.8; 435/243; 435/254.1; 435/255.1; 435/255.2; 435/255.21
(58) Field of Search ................ 424/400, 439, 424/464, 489, 780, 800; 435/173.1, 173.8, 243, 254.1, 255.1, 255.2, 255.21, FOR 100, FOR 114

(56) References Cited

U.S. PATENT DOCUMENTS

| 4,081,367 A | 3/1978 | Hulls et al. .......... 210/610 |
| 4,183,807 A | 1/1980 | Yoshizawa et al. ...... 210/611 |

(List continued on next page.)

FOREIGN PATENT DOCUMENTS

| CN | 1110317 A | 10/1995 |
| EP | 0041373 | 12/1981 |
| FR | 2222433 | 10/1974 |
| JP | 60028893 | 2/1985 |
| RU | 415983 A | 11/1974 |
| RU | 1071637 | 2/1984 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/070682 | 9/2002 |

OTHER PUBLICATIONS

Binninger, D. M. et al., "Effects of 60Hz AC magnetic fields on gene expression following exposure over multiple cell generations using *Saccharomyces cerevisiae*", *Bioelectrochemistry and Bioenergetics*, 43(1): 83–89 (1997).

Deguchi, T. et al., "Nylon biodegradation by lignin–degrading fungi", *Applied and Environmental Microbiology*, 63(1): 329–331 (1997).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material–relation to food processing", *Radiation Physics and Chemistry*, 45(4):591–607 (1995).

Van Rensburg, P. et al., "Engineering yeast for efficient cellulose degradation", *Yeast*, 14(1):67–76 (1998).

"*Saccharomyces cerevisiae* Meyen ex Hansen", China Catalogue of Cultures/China Committee of Culture Collection for Microorganisms (CCCCM), "www.im.ac.cn/database/YEAST.y122.htm", Apr. 24, 1996, retrieved on Nov. 27, 2002.

(List continued on next page.)

*Primary Examiner*—Thurman K. Page
*Assistant Examiner*—Charesse Evans
(74) *Attorney, Agent, or Firm*—Fish & Neave; James F. Haley, Jr.; Z. Ying Li

(57) ABSTRACT

Compositions comprising a plurality of yeast cells, wherein said plurality of yeast cells have been cultured in the presence of an alternating electric field having a specific frequency and a specific field strength for a period of time sufficient to increase the capability of said plurality of yeast cells to improve the memory of a mammal. Also included are methods of making such compositions.

9 Claims, 2 Drawing Sheets

U.S. PATENT DOCUMENTS

| | | | |
|---|---|---|---|
| 4,211,645 A | 7/1980 | Zajic et al. | 210/611 |
| 4,559,305 A | 12/1985 | Zajic et al. | 435/243 |
| 4,816,158 A | 3/1989 | Shimura et al. | 210/610 |
| 5,075,008 A | 12/1991 | Chigusa et al. | 210/610 |
| 5,106,594 A | 4/1992 | Held et al. | 422/292 |
| 5,416,010 A | 5/1995 | Langenberg et al. | 435/468 |
| 5,476,787 A | 12/1995 | Yokoyama et al. | 435/262.5 |
| 5,567,314 A | 10/1996 | Chigusa et al. | 210/150 |
| 5,578,486 A | 11/1996 | Zhang | 435/243 |
| 5,707,524 A | 1/1998 | Potter | 210/606 |
| 5,879,928 A | 3/1999 | Dale et al. | 435/264 |
| 6,036,854 A | 3/2000 | Potter | 210/177 |
| 6,391,617 B1 | 5/2002 | Cheung | 435/254.21 |
| 6,391,618 B1 | 5/2002 | Cheung | 435/255.1 |
| 6,391,619 B1 | 5/2002 | Cheung | 435/255.1 |
| 6,436,695 B1 | 8/2002 | Cheung | 435/254.21 |
| 6,440,713 B1 | 8/2002 | Cheung | 435/173.1 |
| 2002/0123127 A1 | 9/2002 | Cheung | 435/254.21 |
| 2002/0123129 A1 | 9/2002 | Cheung | 435/254.21 |
| 2002/0123130 A1 | 9/2002 | Cheung | 435/262.5 |

OTHER PUBLICATIONS

K. Asami et al., "Real–Time Monitoring of Yeast Cell Division by Dielectric Spectroscopy", *Biophysical Journal*, 76, pp. 3345–3348 (1999).

E.K. Balcer–Kubiczek et al., "Expression Analysis of Human HL60 Cells Exposed to 60 Hz Square–or Sine–Wave Magnetic Fields", *Radiation Research*, 153, pp. 670–678 (2000).

C.A.L. Bassett et al., "Beneficial Effects of Electromagnetic Fields", *Journal of Cellular Biochemistry*, 51, pp. 387–393 (1993).

P. Conti et al., "Effect of Electromagnetic Fields on Several CD Markers and Transcription and Expression of CD4", *Immunobiology*, 201, pp. 36–48 (1999).

A.M. Gonzalez et al., "Effects of an Electric Field of Sinusoidal Waves on the Amino Acid Biosynthesis by Azotobacter", *Z. Naturforsch*, 35, pp. 258–261 (1980).

E.M. Goodman et al., "Effects of Electromagnetic Fields on Molecular and Cells", *International Review of Cytology*, 158, pp. 279–339 (1995).

T. Grospietsch et al., "Stimulating Effects of Modulated 150 MHz Electromagnetic Fields on the Growth of *Escherichia coli* in a Cavity Resonator", *Bioelectrochemistry and Bioenergetics*, 37, pp. 17–23 (1995).

W. Grundler et al., "Nonthermal Effects of Millimeter Microwaves on Yeast Growth", *Z. Naturforsch*, 33, pp. 15–22 (1978).

W. Grundler et al., "Mechanisms of Electromagnetic Interaction with Cellular Systems", *Naturwissenschaften*, 79, pp. 551–559 (1992).

O.I. Ivaschuk et al., "Exposure of Nerve Growth Factor–Treated PC12 Rat Pheochromocytoma Cells to a Modulated Radiofrequency Field at 836.55 MHz: Effects on c–*jun* and c–*fos* Expression", *Bioelectromagnetics*, 18, pp. 223–229 (1997).

F. Jelínek et al., "Microelectronic Sensors for Measurement of Electromagnetic Fields of Living Cells and Experimental Results", *Bioelectrochemistry and Bioenergetics*, 48, pp. 261–266 (1999).

A. Lucy–Hulbert et al., "Biological Responses to Electromagnetic Fields", *FASEB Journal*, 12, pp. 395–420 (1998).

C.R. Libertin et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91–96 (1994).

H. Lin et al., "Specific Region of the c–*myc* Promoter Is Responsive to Electric and Magnetic Fields", *Journal of Cellular Biochemistry*, 54, pp. 281–288 (1994).

H. Lin et al., "Magnetic Field Activation of Protein–DNA Binding", *Journal of Cellular Biochemistry*, 70, pp. 297–303 (1998).

L.I. Loberg et al., "Expression of Cancer–Related Genes in Human Cells Exposed to 60 Hz Magnetic Fields", *Radiation Research*, 153, pp. 679–684 (2000).

R.L. Moore, "Biological Effects of Magnetic Fields: Studies with Microorganisms", *Canadian Journal of Microbiology*, 25, pp. 1145–1151 (1979).

C.A. Morehouse et al., "Exposure of Daudi Cells to Low–Frequency Magnetic Fields Does Not Elevate *MYC*, Steady–State mRNA Levels", *Radiation Research*, 153, pp. 663–669 (2000).

V. Norris et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

G. Novelli et al., "Study of the Effects on DNA of Electromagnetic Fields Using Clamped Homogeneous Electric Field Gel Electrophoresis", *Biomedicine & Pharmacotherapy*, 45, pp. 451–454 (1991).

J.L. Phillips, "Effects of Electromagnetic Field Exposure on Gene Transcription", *Journal of Cellular Biochemistry*, 51, pp. 381–386 (1993).

V. Romano–Spica et al., "Ets1 Oncogene Induction by ELF–Modulated 50 MHz Radiofrequency Electromagnetic FIeld", *Bioelectromagnetics*, 21, pp. 8–18 (2000).

J.E. Trosko, "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

C. Ventura et al., "Elf–pulsed Magnetic Fields Modulate Opioid Peptide Gene Expression in Myocardial Cells", *Cardiovascular Research*, 45, pp. 1054–1064 (2000).

A.M. Woodward et al., "Genetic Programming as an Analytical Tool for Non–linear Dielectric Spectroscopy", *Bioelectrochemistry and Bioenergetics*, 48, pp. 389–396 (1999).

T. Yonetani et al., "Electromagnetic Properties of Hemoproteins", *The Journal of Biological Chemistry*, 247, pp. 2447–2455 (1972).

L. Zhang et al., "Electrostimulation of the Dehydrogenase System of Yeast by Alternating Currents", *Bioelectrochemistry and Bioenergetics*, 28, pp. 341–353 (1992).

N. Agarwal, et al., "Selection of *Saccharomyces cerevisiae* strains for use as a microbial feed additive," *Letters in Applied Microbiology*, 31, 270–273 (2000).

C. Dufresne, et al., "Tea, Kombucha, and health: a review," *Food Research International*, 33, 409–421 (2000).

E.M. Goodman, et al., "Effects of electromagnetic fields on molecules and cells," *International Review of Cytology, Academic Press*, 158, 279–338 (1995).

C.J. Greenwalt, et al., "Kombucha, the fermented tea: microbiology, composition, and claimed health effects," *Journal of Food Protection*, 63, No. 7, 976–981 (2000).

W. Grundler, et al., "Resonant–like dependence of yeast growth rate on microwave frequencies," *Br. J. Cancer*, 45(5), 206–208 (1982).

C.H. Liu, et al., "The isolation and identification of microbes from a fermented tea beverage, Haipao, and their interactions during Haipao fermentation," *Food Microbiology*, 113, 407–415, (1996).

P. Mayser, et al., "The yeast spectrum of the 'tea fungus Kombucha'," *Mycoses*, 38, 289–295 (1995).

C.T. Ponne, et al., "Interaction of electromagnetic energy with biological material —relation to food processing," *Radiat. Phys. Chem.*, 45(4), 591–607 (1995).

C.M. Surawicz, et al., "The search for a better treatment for recurrent *Clostridium difficile* disease: use of high–does vencomycin combined with *Saccharomyces boulardii*," *Clinical Infections*, 31, 1012–1017 (2000).

J. Van Den Bogaerde, et al., "Immune sensitization to food, yeast and bacteria in Crohn's disease," *Aliment Pharmacol. Ther.*, 15, 1647–1653 (2001).

DIETARY SUPPLEMENTS FOR IMPROVING MEMORY

FIELD OF THE INVENTION

The invention relates to compositions that improve memory and can be taken as dietary supplements. The compositions comprise yeast cells obtainable by growth in electromagnetic fields with specific frequencies and field strengths.

BACKGROUND OF THE INVENTION

Memory includes the following four processes: identification and memorization, information storage, recognition and recollection. Identification is the process of imprinting the object or experience in the brain. Information storage is the process of strengthening and maintaining the imprint. Recognition is the process of establishing a connection between a stimulus and the imprint. Recollection is the process of activating the imprint. In addition, memory can be divided into three systems: sense recording, short-term information storage and long-term information storage.

Brain cells can deteriorate after exposure to extensive stress and toxic compounds. This deterioration in turn affects memory. The intake of food that is contaminated with chemical fertilizers, pesticides and chemicals is one way in which the brain is exposed to toxic compounds. Toxic compounds can also be inhaled from the air. It is thus desirable to provide a composition effective in alleviating brain cell damage and improving memory.

SUMMARY OF THE INVENTION

This invention is based on the discovery that certain yeast cells can be activated by electromagnetic fields having specific frequencies and field strengths to produce substances that assist in the recovery of memory deterioration and brain cell damage, as well as improve the memory of a functionally normal brain. The composition of this invention can be taken as dietary supplements in the form of health drinks or pills.

This invention embraces a composition comprising a plurality of yeast cells that have been cultured in an alternating electric field having a frequency in the range of about 12000 to 12100 MHz, and a field strength in the range of about 50 to 600 mV/cm. In one embodiment, the frequency is in the range of 12020–12090 MHz. In another embodiment, the field strength is in the range of 50 to 480 mV/cm. The yeast cells are cultured in the alternating electric field for a period of time sufficient to increase the capability of said plurality of yeast cells to improve the memory of a mammal, as compared to unactivated yeast cells. In one embodiment, the frequency and/or the field strength of the alternating electric field can be altered within the aforementioned ranges during said period of time. In other words, the yeast cells can be exposed to a series of electromagnetic fields. An exemplary period of time is about 5 to 150 hours. In one embodiment, the period of time is 50–77 hours. Included within this invention are also methods of making these compositions.

Yeast cells that can be included in this composition can all be obtained from the China General Microbiological Culture Collection Center ("CGMCC"), a depository recognized under the Budapest Treaty (China Committee for Culture of Microorganisms, Institute of Microbiology, Chinese Academy of Sciences, Haidian, P.O. BOX 2714, Beijing, 100080, China). Useful yeast species include, but are not limited to, *Schizosaccharomyces pombe, Saccharomyces sake, Saccharomyces uvarum, Saccharomyces rouxii, Saccharomyces carlsbergensis* Hansen, *Rhodotorula aurantiaca* and *Saccharomyces cerevisiae*. For instance, the yeast cells can be of the strain AS2.502. In one embodiment, the yeast cells are from the strains selected from the group consisting of AS 2.501, AS2.502, AS2.503, AS2.504, AS2.535, AS2.558, AS2.560, AS2.561 and AS2.562. Other useful yeast species are illustrated in Table 1.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

Other features and advantages of the invention will be apparent from the following detailed description, and from the claims.

DETAILED DESCRIPTION OF THE INVENTION

Figure 1:
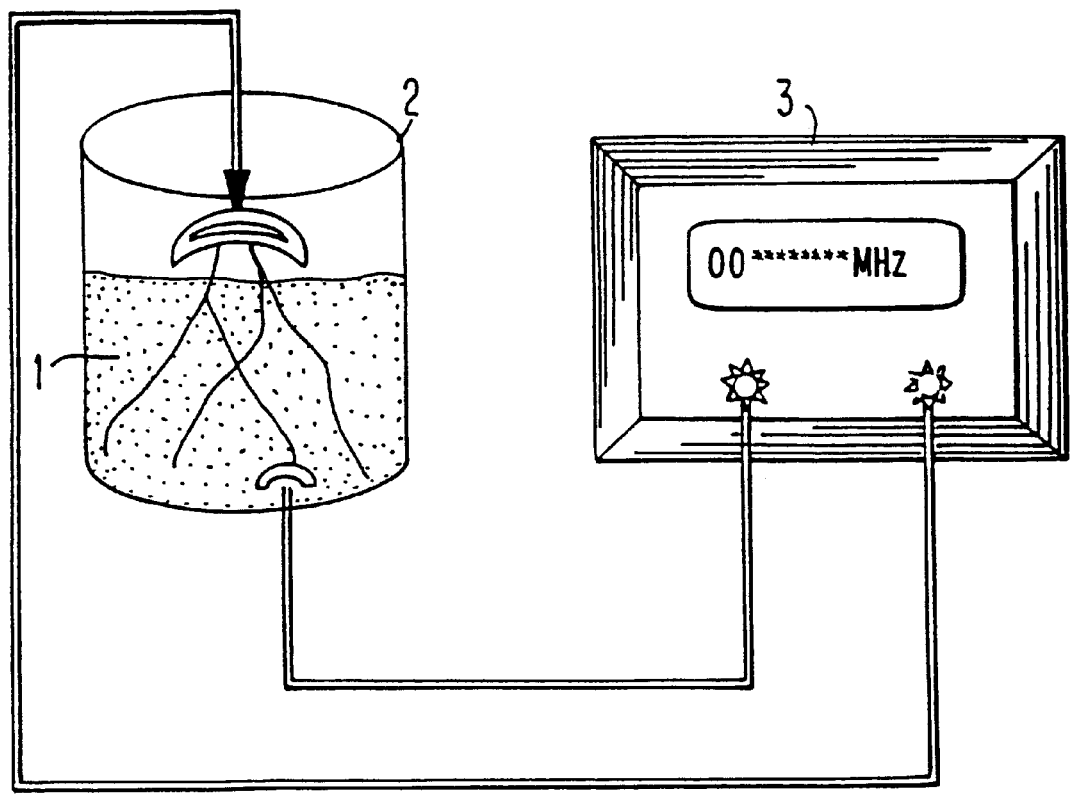
FIG. 1 is a schematic diagram showing an exemplary apparatus for activating yeast cells using electromagnetic fields. 1: yeast culture; 2: container; 3: power supply.

This invention is based on the discovery that certain yeast strains can be activated by electromagnetic fields ("EMF") having specific frequencies and field strengths to produce agents useful in improving memory. Yeast compositions containing activated yeast cells can be used as dietary supplements in the form of, e.g., health drinks or pills.

Since the activated yeast cells contained in these yeast compositions have been cultured to endure acidic conditions of pH 2.5–4.2, the compositions are stable in the stomach and can pass on to the intestines. Once in the intestines, the yeast cells are ruptured by various digestive enzymes, and the agents useful in improving memory are released and readily absorbed.

Without being bound by any theory or mechanism, the inventor believes that EMFs activate or enhance the expression of a gene or a set of genes in the yeast cells such that the yeast cells become active or more efficient in performing certain metabolic activities which lead to the production of agents that improve memory.

I. Yeast Strains Useful in the Invention

The types of yeasts useful in this invention include, but are not limited to, yeasts of the genera Saccharomyces, Schizosaccharomyces and Rhodotorula.

Exemplary species within the above-listed genera include, but are not limited to, the species illustrated in Table 1. Yeast strains useful in this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with the accession numbers of CGMCC) are illustrated in Table 1. In general, yeast strains preferred in this invention are those used for fermentation in the food and wine industries. As a result, compositions containing these yeast cells are safe for human consumption. Although it is preferred, the preparation of the yeast compositions of this invention is not limited to starting with a pure strain of yeast. A yeast composition of the invention may be produced by culturing a mixture of yeast cells of different species or strains.

TABLE 1

Exemplary Yeast Strains

*Saccharomyces cerevisiae* Hansen

| ACCC2034 | ACCC2035 | ACCC2036 | ACCC2037 | ACCC2038 |
|---|---|---|---|---|
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var. *ellipsoideus* (Hansen) Dekker

| ACCC2043 | AS2.2 | AS2.3 | AS2.8 | AS2.53 |
|---|---|---|---|---|
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| AS2.131 | AS2.213 | | | |

*Saccharomyces delbrueckii*

| AS2.285 | | | | |

*Saccharomyces delbrueckii* Lindner ver. *mongolicus* (Saito) Lodder et van Rij

| AS2.209 | AS2.1157 | | | |

*Saccharomyces exiguous* Hansen

| AS2.349 | AS2.1158 | | | |

*Saccharomyces fermentati* (Saito) Lodder et van Rij

| AS2.286 | AS2.343 | | | |

TABLE 1-continued

Exemplary Yeast Strains

*Saccharomyces logos* van laer et Denamur ex Jorgensen

| AS2.156 | AS2.327 | AS2.335 | | |
|---|---|---|---|---|

*Saccharomyces mellis* (Fabian et Quinet) Lodder et kreger van Rij

| AS2.195 | | | | |

*Saccharomyces mellis* Microellipsoides Osterwalder

| AS2.699 | | | | |

*Saccharomyces oviformis* Osteralder

| AS2.100 | | | | |

*Saccharomyces rosei* (Guilliermond) Lodder et Kreger van Rij

| AS2.287 | | | | |

*Saccharomyces rouxii* Boutroux

| AS2.178 | AS2.180 | AS2.370 | AS2.371 | |

*Saccharomyces sake* Yabe

| ACCC2045 | | | | |

*Candida arborea*

| AS2.566 | | | | |

*Candida lambica* (Lindner et Genoud) van. Uden et Buckley

| AS2.1182 | | | | |

*Candida krusei* (Castellani) Berkhout

| AS2.1045 | | | | |

*Candida lipolytica* (Harrison) Diddens et Lodder

| AS2.1207 | AS2.1216 | AS2.1220 | AS2.1379 | AS2.1398 |
| AS2.1399 | AS2.1400 | | | |

*Candida parapsilosis* (Ashford) Langeron et Talice Var. *intermedia* Van Rij et Verona

| AS2.491 | | | | |

*Candida parapsilosis* (Ashford) Langeron et Talice

| AS2.590 | | | | |

*Candida pulcherrima* (Lindner) Windisch

| AS2.492 | | | | |

*Candida rugousa* (Anderson) Diddens et Lodder

| AS2.511 | AS2.1367 | AS2.1369 | AS2.1372 | AS2.1373 |
| AS2.1377 | AS2.1378 | AS2.1384 | | |

*Candida tropicalis* (Castellani) Berkhout

| ACCC2004 | ACCC2005 | ACCC2006 | AS2.164 | AS2.402 |
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

| AS2.120 | AS2.281 | AS2.1180 | | |

*Crebrothecium ashbyii* (Guilliermond) Routein (*Eremothecium ashbyii* Guilliermond)

| AS2.481 | AS2.482 | AS2.1197 | | |

*Geotrichum candidum* Link

| ACCC2016 | AS2.361 | AS2.498 | AS2.616 | AS2.1035 |
| AS2.1062 | AS2.1080 | AS2.1132 | AS2.1175 | AS2.1183 |

*Hansenula anomala* (Hansen)H et P sydow

| ACCC2018 | AS2.294 | AS2.295 | AS2.296 | AS2.297 |
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

TABLE 1-continued

Exemplary Yeast Strains

| | | | | |
|---|---|---|---|---|
| | *Hansenula arabitolgens* Fang | | | |
| AS2.887 | | | | |
| | *Hansenula jadinii* (A. et R Sartory Weill et Meyer) Wickerham | | | |
| ACCC2019 | | | | |
| | *Hansenula saturnus* (Klocker) H et P sydow | | | |
| ACCC2020 | | | | |
| | *Hansenula schneggii* (Weber) Dekker | | | |
| AS2.304 | | | | |
| | *Hansenula subpelliculosa* Bedford | | | |
| AS2.740 | AS2.760 | AS2.761 | AS2.770 | AS2.783 |
| AS2.790 | AS2.798 | AS2.866 | | |
| | *Kloeckera apiculata* (Reess emend. Klocker) Janke | | | |
| ACCC2022 | ACCC2023 | AS2.197 | AS2.496 | AS2.714 |
| ACCC2021 | AS2.711 | | | |
| | *Lipomycess starkeyi* Lodder et van Rij | | | |
| AS2.1390 | ACCC2024 | | | |
| | *Pichia farinosa* (Lindner) Hansen | | | |
| ACCC2025 | ACCC2026 | AS2.86 | AS2.87 | AS2.705 |
| AS2.803 | | | | |
| | *Pichia membranaefaciens* Hansen | | | |
| ACCC2027 | AS2.89 | AS2.661 | AS2.1039 | |
| | *Rhodosporidium toruloides* Banno | | | |
| ACCC2028 | | | | |
| | *Rhodotorula glutinis* (Fresenius) Harrison | | | |
| AS2.2029 | AS2.280 | ACCC2030 | AS2.102 | AS2.107 |
| AS2.278 | AS2.499 | AS2.694 | AS2.703 | AS2.704 |
| AS2.1146 | | | | |
| | *Rhodotorula minuta* (Saito) Harrison | | | |
| AS2.277 | | | | |
| | *Rhodotorula rubar* (Demme) Lodder | | | |
| AS2.21 | AS2.22 | AS2.103 | AS2.105 | AS2.108 |
| AS2.140 | AS2.166 | AS2.167 | AS2.272 | AS2.279 |
| AS2.282 | ACCC2031 | | | |
| | *Rhodotorula aurantiaca* (Saito) Lodder | | | |
| AS2.102 | AS2.107 | AS2.278 | AS2.499 | AS2.694 |
| AS2.703 | AS2.704 | AS2.1146 | | |
| | *Saccharomyces carlsbergensis* Hansen | | | |
| AS2.113 | ACCC2032 | ACCC2033 | AS2.312 | AS2.116 |
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |
| | *Saccharomyces uvarum* Beijer | | | |
| IFFI1023 | IFFI1032 | IFFI1036 | IFFI1044 | IFFI1072 |
| IFFI1205 | IFFI1207 | | | |
| | *Saccharomyces willianus* Saccardo | | | |
| AS2.5 | AS2.7 | AS2.119 | AS2.152 | AS2.293 |
| AS2.381 | AS2.392 | AS2.434 | AS2.614 | AS2.1189 |
| | *Saccharomyces sp.* | | | |
| AS2.311 | | | | |
| | *Saccharomycodes ludwigii* Hansen | | | |
| ACCC2044 | AS2.243 | AS2.508 | | |

TABLE 1-continued

Exemplary Yeast Strains

| | | | | |
|---|---|---|---|---|
| | *Saccharomycodes sinenses* Yue | | | |
| AS2.1395 | | | | |
| | *Schizosaccharomyces octosporus* Beijerinck | | | |
| ACCC2046 | AS2.1148 | | | |
| | *Schizosaccharomyces pombe* Lindner | | | |
| ACCC2047 | ACCC2048 | AS2.214 | AS2.248 | AS2.249 |
| AS2.255 | AS2.257 | AS2.259 | AS2.260 | AS2.274 |
| AS2.994 | AS2.1043 | AS2.1149 | AS2.1178 | IFFI1056 |
| | *Sporobolomyces roseus* Kluyver et van Niel | | | |
| ACCC2049 | ACCC2050 | AS2.19 | AS2.962 | AS2.1036 |
| ACCC2051 | AS2.261 | AS2.262 | | |
| | *Torulopsis candida* (Saito) Lodder | | | |
| AS2.270 | ACCC2052 | | | |
| | *Torulopsis famta* (Harrison) Lodder et van Rij | | | |
| ACCC2053 | AS2.685 | | | |
| | *Torulopsis globosa* (Olson et Hammer) Lodder et van Rij | | | |
| ACCC2054 | AS2.202 | | | |
| | *Torulopsis inconspicua* Lodder et Kreger van Rij | | | |
| AS2.75 | | | | |
| | *Trichosporon behrendii* Lodder et Kreger van Rij | | | |
| ACCC2056 | AS2.1193 | | | |
| | *Trichosporon capitatum* Diddens et Lodder | | | |
| ACCC2056 | AS2.1385 | | | |
| | *Trichosporon cutaneum* (de Beurm et al.) Ota | | | |
| ACCC2057 | AS2.25 | AS2.570 | AS2.571 | AS2.1374 |
| | *Wickerhamia fluorescens* (Soneda) Soneda | | | |
| ACCC2058 | AS2.1388 | | | |

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag—AgCl electrodes in solutions rich in chloride ions, and run at as low a voltage as possible. For general review, see Goodman et al., *Effects of EMF on Molecules and Cells,* International Review of Cytology, A Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 12000 MHz to 12100 MHz. Exemplary frequencies include 12034, 12041, 12052, 12064 and 12069 MHz.

The field strength of the electric field useful in this invention ranges from about 50 to 600 mV/cm (e.g., 50–100, 120–200, 260–400 or 450–490 mV/cm). Exemplary field strengths include 65, 122, 142, 160, 168, 188, 280, 300, 335, 387, 367 and 475 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9 or 10 EMFs in a series.

Although the yeast cells can be activated after even a few hours of culturing in the presence of an EMF, it may be preferred that the compositions comprising activated yeast cells be allowed to multiply and grow in the presence of the EMF(s) for a total of 50 to 77 hours.

FIG. 1 illustrates an exemplary apparatus for generating alternating electric fields. An electric field of a desired frequency and intensity can be generated by an AC source (3) capable of generating an alternating electric field, preferably in a sinusoidal wave form, in the frequency range of 5 to 20,000 MHz. Signal generators capable of generating signals with a narrower frequency range can also be used. If desired, a signal amplifier can also be used to increase the output. The culture container (2) can be made from a non-conductive material, e.g., glass, plastic or ceramic. The cable connecting the culture container (2) and the signal generator (3) is preferably a high frequency coaxial cable with a transmission frequency of at least 20 Ghz. In one embodiment, the transmission frequency is 30 Ghz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, wire can be 3–5 cm, 5–7 cm, 7–10 cm, 10–15 cm, 15–20 cm, 20–30 cm and from the bottom of the container (2), respectively. The number of metal wires/tubes used can be from 1 to 10 (e.g., 2 to 3). It is recommended, though not mandated, that for a culture having a volume up to 10 L, metal wires/tubes having a diameter of 0.5 to 2 mm be used. For a culture having a volume of 10–100 L, metal wires/tubes having a diameter of 3 to 5 mm can be used. For a culture having a volume of 100–1000 L, metal wires/tubes having a diameter of 6 to 15 mm can be used. For a culture having a volume greater than 1000 L, metal wires/tubes having a diameter of 20–25 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients that can be assimilated by yeast cells. Complex carbon-containing substances in a suitable form (e.g., carbohydrates such as sucrose, glucose, dextrose, maltose, starch, xylose; mannitol) can be the carbon sources for yeast cells. The exact quantity of the carbon sources can be adjusted in accordance with the other ingredients of the medium. In general, the amount of carbon-containing substances varies between about 0.5% and 10% by weight of the medium, and preferably between about 1% and 5%, and most preferably between about 1.3–2.2%. These carbon sources can be used individually or in combination. Among the inorganic salts which can be added to a culture medium are the customary salts capable of yielding sodium, potassium, calcium, phosphate, sulfate, carbonate, and like ions. Non-limiting examples of nutrient inorganic salts are $(NH_4)_2HPO_4$, $CaCO_3$, $KH_2PO_4$, $K_2HPO_4$, $MgSO_4$, NaCl, and $CaSO_4$.

IV. Electromagnetic Activation of Yeast Cells

To activate or enhance the innate ability of yeast cells to improve memory, these cells can be cultured in an appropriate medium under sterile conditions at 20° C.–35° C. (e.g., 28–32° C.) for a sufficient amount of time, e.g., 5–150 hours (e.g., 50–77 hours), in an alternating electric field or a series of alternating electric fields as described above.

An exemplary set-up of the culture process is depicted in FIG. 1 (see above). An exemplary culture medium contains the following in per 1000 ml of sterile water: 15 g of soluble starch, 10 g of mannitol, 0.25 g of $K_2HPO_4$, 0.2 g of $KH_2PO_4$, 0.2 g of $MgSO_4.7H_2O$, 0.3 g of NaCl, 0.1 g of $CaSO_4.2H_2O$, 3.0 g of $CaCO_3.5H_2O$, 0.4 g of yeast paste. Yeast cells of the desired strains are then added to the culture medium to form a mixture containing $1 \times 10^8$ yeast cells per 1000 ml of culture medium. The yeast cells can be of any of the strains listed in Table 1. In one embodiment, the strain is *Saccharomyces cerevisiae* Hansen A2.502. The mixture is then added to the apparatus of FIG. 1.

The activation process of the yeast cells involves the following steps: b 1) maintaining the temperature of the activation apparatus at 20–35° C., (e.g., 28–32° C.), culturing the yeast cells for 24–36 hours; 2) applying an electric field having a frequency of about 12034 MHz and a field strength of 170–200 mV/cm (e.g., about 188 mV/cm) for 10–15 hours (e.g.,12 hours); 3) maintaining the temperature of the activation apparatus at 28–32° C., culturing the yeast cells for 24–36 hours; 4) then applying an electric field having a frequency of about 12041 MHz and a field strength of 120–200 mV/cm (e.g., about 168 mV/cm) for 24–30 hours (e.g., 28 hours); 5) then applying an electric field having a frequency of about 12052 MHz and a field strength of 320–400 mV/cm (e.g., about 367 mV/cm) for 18–20 hours (e.g., 19 hours); 6) then applying an electric field having a frequency of about 12064 MHz and a field strength of 450–490 mV/cm (e.g., about 475 mV/cm) for 7–10 hours (e.g., 8 hours); 7) then applying an electric field having a frequency of about 12069 MHz and a field strength of 290–320 mV/cm (e.g., about 300 mV/cm) for 9–12 hours (e.g., 10 hours); and 7) finally lyophilizing the compositions comprising activated yeast cells to form a powder and storing the powder at 4° C. Preferably, the concentration of the lyophilized yeast cells are more than $10^{10}$ cells/g.

V. Acclimatization of Yeast Cells To the Gastric Environment

Because the yeast compositions of this invention must pass through the stomach before reaching the small intestine, where the effective components are released from these yeast cells, it is preferred that these yeast cells be cultured under acidic conditions to acclimatize the cells to the gastric juice. This acclimatization process results in better viability of the yeasts in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture is then cultured first in the presence of an alternating electric field having a frequency of about 12064 MHz and a field strength of 350–400 mV/cm (e.g., about 387 mV/cm) at about 28 to 20 32° C. for 45 hours. The resultant yeast cells are further incubated in the presence of an alternating electric field having a frequency of about 12069 MHz and a field strength of 260–300 mV/cm (e.g., about 280 mV/cm) at about 28 to 32° C. for 22 hours. The resulting acclimatized yeast cells are then either dried and stored in powder form ($\geq 10^{10}$ cells/g) at room temperature or in vacuum at 0–4° C.

An exemplary acclimatizing culture medium is made by mixing 700 ml of fresh pig gastric juice and 300 ml of wild Chinese hawthorn extract. The pH of the acclimatizing culture medium is adjusted to 2.5 with 0.1 M hydrochloric acid and 0.2 M Potassium biphthalate. The fresh pig gastric juice is prepared as follows. At about 4 months of age, newborn Holland white pigs are sacrificed, and the entire contents of their stomachs are retrieved and mixed with 2000 ml of water under sterile conditions.

The mixture is then allowed to stand for 6 hours at 4° C. under sterile conditions to precipitate food debris. To prepare the wild Chinese hawthorn extract, 500 g of fresh wild Chinese hawthorn is dried under sterile conditions to reduce the water content ($\leq 8\%$). The dried fruit is then ground ($\geq 20$ mesh) and added to 1500 ml of sterile water. The mixture is allowed to stand for 6 hours at 4° C. under sterile conditions. The supernatant is collected to be used in the acclimatizing culture medium.

VI. Manufacture of Yeast Compositions

Figure 2:
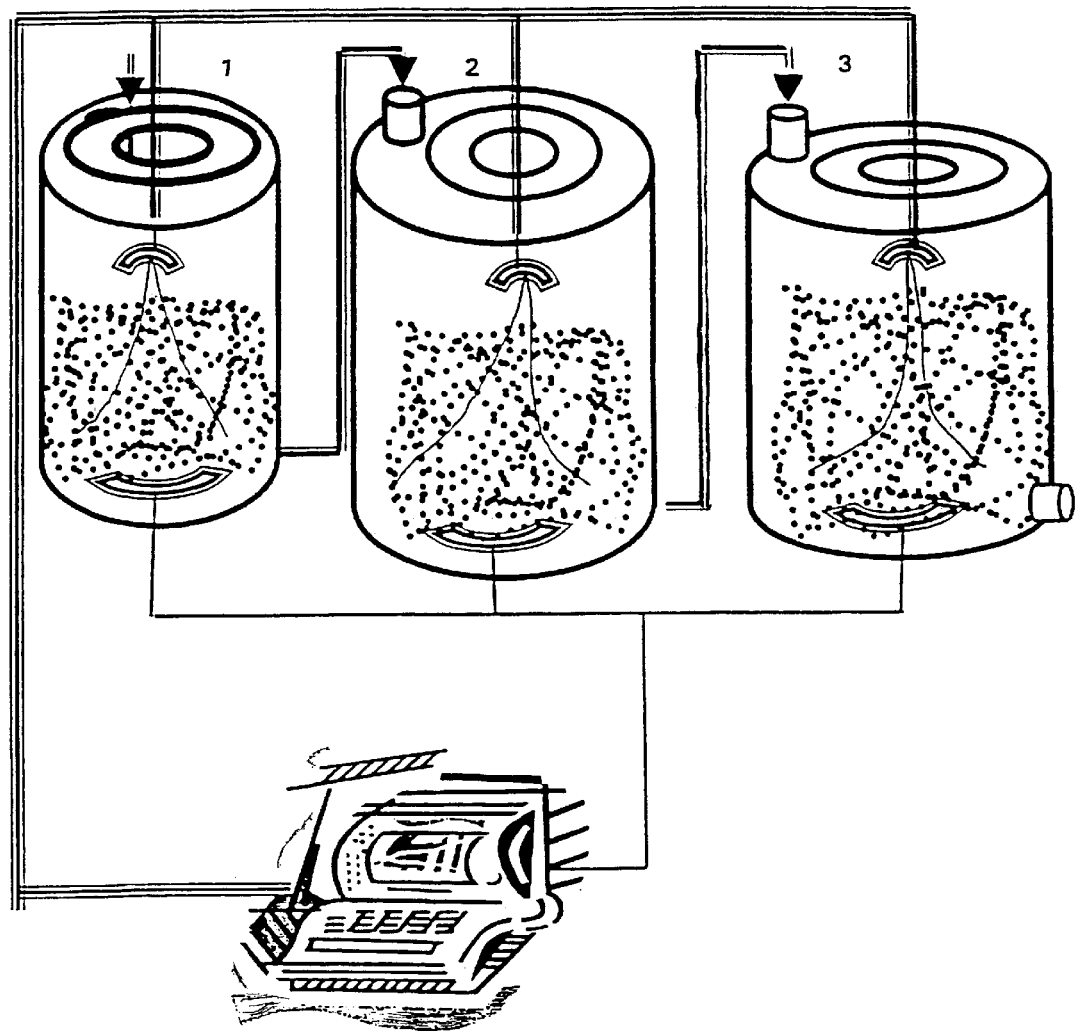
FIG. 2 is a schematic diagram showing an exemplary apparatus for making yeast compositions of the invention. The apparatus comprises a signal generator and interconnected containers 1, 2 and 3.

To prepare the yeast compositions of the invention, an apparatus depicted in FIG. 2 or an equivalent thereof can be used. This apparatus includes a first container (1), a second container (2), and a third container (3), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of fruit extracts from *Schisandra chinensis* Baill (wu wei zi), and 100 L of soy bean extracts. To prepare hawthorn, jujube and wu wei zi extracts, the fresh fruits are washed and dried under sterile conditions to reduce the water content to no higher than 8%. One hundred kilograms of the dried fruits are then ground ($\geq 20$ mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and centrifuged at 1000 rpm to remove insoluble residues. Once the mixed fruit extract solution is prepared, the solution is sterilized at 121° C. for 30 minutes, and cooled to 40° C. before use.

One thousand grams of the activated yeast powder prepared as described above (Section V, supra) is added to 1000 L of the mixed fruit extract solution, and the yeast solution is transferred to the first container (1) shown in FIG. 2. The yeast cells are then cultured in the presence of an alternating electric field having a frequency of about 12064 MHz and a field strength of about 300–350 mV/cm (e.g., about 335 mV/cm) at 28–32° C. under sterile conditions for 12 hours. The yeast cells are further incubated in an alternating electric field having a frequency of about 12069 MHz and a field strength of 280–350 mV/cm (e.g., about 300 mV/cm). The culturing continues for another 10 hours.

The yeast culture is then transferred from the first container (1) to the second container (2) (if need be, a new batch of yeast culture can be started in the now available first container (1)), and subjected to an alternating electric field having a frequency of about 12064 MHz and a field strength of 120–150 mV/cm (e.g., about 142 mV/cm) for six hours. Subsequently the frequency and field strength of the electric field are changed to about 12069 MHz and 140–180 mV/cm (e.g., about 160 mV/cm), respectively. The culturing continues for another eight hours.

The yeast culture is then transferred from the second container (2) to the third container (3), and subjected to an alternating electric field having a frequency of about 12064 MHz and a field strength of 50–80 mV/cm (e.g., about 65 mV/cm) for six hours. Subsequently the frequency and field strength of the electric field are changed to about 12069 MHz and 110–140 mV/cm (e.g., about 122 mV/cm), respectively. The culturing continues for another ten hours.

The yeast culture from the third container (3) can then be packaged into vacuum sealed bottles for use as dietary supplement. The dietary supplement can be taken 3–4 times daily at 30–60 ml each time for a period of three months (10–30 minutes before meals and at bedtime). If desired, the final yeast culture can also be dried within 24 hours and stored in powder form.

In one embodiment, the compositions of the invention can also be administered intravenously or peritoneally in the form of a sterile injectable preparation. Such a sterile preparation is prepared as follows. A sterilized health drink composition is first treated under ultrasound (1000 Hz) for 10 minutes and then centrifuged at 4355 rpm for another 10 minutes. The resulting supernatant is adjusted to pH 7.2–7.4 using 1 M NaOH and subsequently filtered through a membrane (0.22 μm for intravenous injection and 0.45 μm for peritoneal injection) under sterile conditions. The resulting sterile preparation is submerged in a 35–38° C. water bath for 30 minutes before use.

VII. EXAMPLES

The following examples are meant to illustrate the methods and materials of the present invention. Suitable modifications and adaptations of the described conditions and parameters which are obvious to those skilled in the art are within the spirit and scope of the present invention.

The activated yeast compositions used in the following experiments were prepared as described above, using *Saccharomyces cerevisiae* Hansen AS2.502 cultured in the presence of an alternating electric field having the electric field frequency and field strength exemplified in the parentheses following the recommended ranges. Control yeast compositions were those prepared in the same manner except that the yeast cells were cultured in the absence of EMFs. Unless otherwise indicated, all yeast compositions and the corresponding controls were administered to the animals by intragastric feeding.

Example 1

Mouse Platform Leaping Experiment

In this experiment, mice were first trained to carry out a task through conditioned reflex. The mice were tested again after a period of time for their ability to carry out the task.

The apparatus used in this experiment comprised a rectangular box, in which the bottom was covered with parallel copper railings. Each copper railing was 0.5 cm apart from the neighboring ones. The copper railings were connected to an electric source, and the voltage was controlled by a transformer. A round platform having a height and diameter of 4.5 cm was placed at the left rear end of each copper railing. Food such as fried soybean powder was placed on the copper railings.

The mice were first placed in the box for 3 minutes for acclimatization. Immediately after the mice started competing for food, a 36 V alternating current was applied to the copper railings. A normal reaction of the mice was to leap back to the platform to avoid the electric shock. Due to the temptation of food, a majority of the mice repeatedly leaped back to the copper railings, and then returned to the platform when they were electro-shocked. During the 5 minute training, the number of times each mice was electro-shocked was recorded. This number was also called the number of errors. After 24 hours, the training was resumed for three minutes. During this period, the number of mice electro-shocked, the time period before each mouse made the first leap to the copper railings (lag period), and the number of errors for each mouse were recorded.

Thirty-six NIH-grade mice were divided into three groups of 12. Each mouse in groups A, B and C was administered daily 2 ml of the activated yeast composition, the control yeast composition and saline, respectively. The mice were treated for 6 weeks before the first platform leaping experiment was performed (Table 2). The results of the platform leaping experiment conducted after 24 hours of the first leaping experiment are illustrated in Table 3.

TABLE 2

| Group | Animal number | Lag period (seconds) (x ± SD) | Number of errors (x ± SD) |
|---|---|---|---|
| A | 12 | 92.23 ± 81.23 | 4.13 ± 2.22 |
| B | 12 | 36.54 ± 23.45 | 12.44 ± 4.64 |
| C | 12 | 35.56 ± 18.25 | 12.65 ± 5.82 |

TABLE 3

| Group | Animal number | Lag period (seconds) (x ± SD) | Number of errors (x ± SD) |
|---|---|---|---|
| A | 12 | 87.57 ± 79.54 | 5.22 ± 3.15 |
| B | 12 | 31.33 ± 43.34 | 15.64 ± 6.56 |
| C | 12 | 32.22 ± 39.47 | 14.89 ± 6.55 |

Example 2

Mouse Y-Shaped Maze Experiment

There are various methods for testing the memory of animals. One of the methods involves the use of a Y-shaped maze. See, R. C. Miller et al., Nature, 228, pp. 1107–1108 (1970), incorporated herein by reference. The stem of the Y is the starting point, where a test animal is initially placed. One arm of the maze is connected to a power supply such that an animal entering this arm will be electro-shocked. The other arm of the maze is a safety zone with food.

In this experiment, 36 NIH mice were divided into three equal groups, A, B, and C. All of them were trained in a Y-shaped maze. The mice were first placed in the starting point and were trained to have a normal reaction of escaping to the safety zone when shocked in the electric zone. The mice were trained until they learned to escape from the electric zone to the safety zone 90% of the time.

Twenty-four hours after the training, mice in groups A, B and C were each administered daily 3 ml of the activated yeast composition, the control yeast composition, and saline, respectively, for 6 weeks. At the end of week 6, the mice were placed in the Y-shaped maze again for behavioral observation. The results are shown in Table 4 below.

TABLE 4

| Group | Animal number | Percentage of normal reactions (%) (x ± SD) |
|---|---|---|
| A | 12 | 97.65 ± 11.2 |
| B | 12 | 69.28 ± 28.66 |
| C | 12 | 67.68 ± 25.34 |

This experiment demonstrates that the activated yeast composition enhanced the memory of the test animals, as compared to the control yeast composition and saline.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by an increase in their capability to improve the memory of a mammal as a result of having been cultured in the presence of an alternating electric field having a frequency in the range of 12000 to 12100 MHz and a field strength in the range of 50 to 600 mV/cm, as compared to yeast cells not having been so cultured.

2. The composition of claim 1, wherein the range of the frequency is 12020–12090 MHz.

3. The composition of claim 1, wherein the range of the field strength is 50–480 mV/cm.

4. The composition of claim 1, wherein said yeast cells are of the species selected from the group consisting of Saccharomyces sp, Schizosaccharomyces pombe Lindner, Saccharomyces sake Yabe, Saccharomyces uvarum Beijer, Saccharomyces rouxii Boutroux, Saccharomyces cerevisiae Hansen Var. ellipsoideus, Saccharomyces carlsbergensis Hansen, Rhodotorula aurantiaca Lodder and Saccharomyces cerevisiae Hansen.

5. The composition of claim 1, wherein said yeast cells are of the strain deposited at the China General Microbiological Culture Collection Center with the accession number selected from the group consisting of Saccharomyces cerevisiae Hansen AS2.501, AS2.502, AS2.503, AS2.504, AS2.535, AS2.558, AS2.560, AS2.561 and AS2.562.

6. The composition position of claim 5, wherein said strain is Saccharomyces cerevisiae Hansen AS2.502.

7. The composition of claim 1, wherein the composition is in the form of a tablet, powder or healthdrink.

8. The composition of claim 1, wherein the composition is in the form of a healthdrink.

9. A method of preparing a yeast composition, comprising culturing a plurality of yeast cells in the presence of an alternating electric field having a frequency in the range of 12000 to 12100 MHz and a field strength in the range of 50 to 600 mV/cm, wherein said plurality of yeast cells are characterized by an increase in their capability to improve the memory of a mammal as a result of said culturing as compared to yeast cells not having been so cultured.

* * * * *